(12) United States Patent
Coates et al.

(10) Patent No.: US 7,057,156 B2
(45) Date of Patent: Jun. 6, 2006

(54) SYSTEM AND METHOD FOR INTEGRATED SENSING AND CONTROL OF INDUSTRIAL PROCESSES

(75) Inventors: John Coates, Newtown, CT (US); Fernando Rathgeb, Sharon, MA (US); Rand Stowell, Weld, ME (US)

(73) Assignee: MicroSpectral Sensing LLC, South Portland, ME (US)

( * ) Notice: Subject to any disclaimer, the term of this patent is extended or adjusted under 35 U.S.C. 154(b) by 68 days.

(21) Appl. No.: 10/913,819

(22) Filed: Aug. 6, 2004

(65) Prior Publication Data

US 2005/0088653 A1    Apr. 28, 2005

Related U.S. Application Data

(60) Provisional application No. 60/494,977, filed on Aug. 14, 2003.

(51) Int. Cl.
*G01J 3/50* (2006.01)
(52) U.S. Cl. .................. 250/226; 250/216
(58) Field of Classification Search ............ 250/226, 250/216, 214.1, 574, 573, 373, 372; 356/451, 356/436, 440
See application file for complete search history.

(56) References Cited

U.S. PATENT DOCUMENTS

| | | | | |
|---|---|---|---|---|
| 5,512,757 A | * | 4/1996 | Cederstrand et al. | 250/373 |
| 6,559,941 B1 | * | 5/2003 | Hammer | 356/319 |

* cited by examiner

*Primary Examiner*—Que T. Le
(74) *Attorney, Agent, or Firm*—Gesmer Updegrove LLP (57) ABSTRACT

An integrated spectral sensing system includes a spectral engine comprising an optical filter assembly bonded to an energy sensitive array. The optical filter assembly and energy sensitive array collectively configured to sense energy transmitted through the optical filter assembly and to generate data based on the sensed energy. An energy source generates energy for impingement upon the spectral engine. A sample interface has a chamber for containing a sample, sized and configured to match the size and configuration of the spectral engine and the energy source. The sample interface is disposed between the spectral engine and the energy source, and configured so that energy from the energy source passes through the sample and impinges upon the spectral engine. Data generated by the energy sensitive array is collected, manipulated, and stored. The collected data is communicated.

12 Claims, 8 Drawing Sheets

Elements and an Example Embodiment of a Spectral Sensing Engine: Integrated Source, Sample Interface, Spectral Analyzer and Detector

Figure 1

Example Combinations of Optical Filters and Detector Components Used for Spectral Sensing Figure 2A: Direct Coupling of Optical Filters and the Detector Array (LVF Version Illustrated)

Figure 2B: Example Integrated Detector Array Component With Filter Matrix

Figure 2C: Example Integrated Detector Array Component Mounted on Flex Connector

SYSTEM AND METHOD FOR INTEGRATED SENSING AND CONTROL OF INDUSTRIAL PROCESSES

CROSS REFERENCE TO RELATED APPLICATION

The present application claims the priority benefit of U.S. provisional patent application Ser. No. 60/494,977, filed Aug. 14, 2003, entitled "SYSTEM AND METHOD FOR INTEGRATED SENSING AND CONTROL OF INDUSTRIAL PROCESSES" of the same named inventors and assigned to a common assignee. The entire contents of that prior application are incorporated herein by reference.

BACKGROUND OF THE INVENTION

1. Field of the Invention

The present invention relates to a miniaturized integrated spectral sensor, with integrated sensed signal conditioning, signal exchange, and integration into a modular sampling system. The sensed information is converted into a meaningful format for process control and is distributed via standard hardwired or wireless communications protocols.

2. Background

Two related aspects of industrial process improvement include the need to understand the process itself, and control of the process based upon that understanding. In particular, it is important to be able to determine the characteristics or parameters at each stage of the process and for the final output of a process, such as the chemical composition, temperature, and/or pressure of reactants used to make a chemical compound, for example. Based upon that information, it is important to be able to adjust the process, such as increasing process temperature, or changing the ratio of reactants, for example, if the output information deviates from an established set of parameters. The inability to monitor the process usually means that there is a risk of low quality product, which results in the need to make corrections, after the product has been made. This is inefficient, and leads to a high level of wastage, which can be compounded by environmental issues.

There are two established approaches to the monitoring of a process for chemical composition or physical properties. They are the extraction of grab samples followed by remote analysis at a suitable control laboratory, and the use of on-line instrumentation. The first option is inefficient and is not effective for control purposes. The second option is usually expensive, and as a result, it is normal to implement a single analyzer at the end of the process. This has limited value for good process control because it is too late in the process to make meaningful adjustments. For a complex process, the ideal situation is to have a multiplicity of measurement points and to monitor the process from the raw material through to the final product. This has to be cost effective to make the implementation of multiple sensing points worthwhile. One solution with optical instrumentation is to use a single analyzer but to multiplex the stream or the optical output. While this is an option, it has risks because it lacks redundancy—one instrument controlling an entire process, and also it is limited in terms of its response, dependent on the number of points being measured (measurements are made sequentially, not in parallel). The present invention uses multiple, miniaturized, low cost spectral sensing devices, a major advancement in measurement opportunity over the status quo, and overcomes issues related to a lack of redundancy. In fact, one may use a redundancy of the sensing devices to ensure maximum efficiency in the event of the failure of a single sensing device. Each device is intended to provide the functionality of a normal analyzer, such as a spectrophotometer, but at reduced cost, and with a significantly reduced size for the total package. While small format sensors exist and are used for standard physical measurements (such as pressure, temperature and flow), these traditional sensors are limited in functionality, and are normally based on changes in electrical properties. The spectral sensing component of the present invention is based on existing optical sensing technology modified for the present purpose. An example component has been marketed as a commercial device by OCLI (a JDS Uniphase company), known as a MicroPac. The device was not produced in a form that was compatible with the proposed application, and was intended only for lab-based experiments that demonstrated feasibility. LVF systems based on a silicon photodiode array can offer spectral ranges of 360 nm to 700 nm (visible) and 600 nm to 1100 nm (short wave near Infrared (NIR)). The original MicroPac device had a complex construction featuring a gradient index (GRIN) lens as an optical interface between the filter and the photodiode assembly. This was required to preserve the spectral resolution of the filter because the detector used was an off-the-shelf commercial detector package. The current implementation uses a simpler construction because it is to be produced as an integrated component as part of the detector array fabrication, by the array manufacturer.

When measuring devices are integrated into a process it is normal to employ a sampling system. The sampling system is typically a collection of valves and sample conditioning devices (filters, mixing chambers, temperature control loops, etc.) that extract the sample from the main stream, and present the sample in an ideal format to the measurement system. Effectively, this is a sample management system, which can include the components to perform reagent-based chemistry for situations where the sensing system requires chemical modification to the sample stream. Traditionally, this collection of valves and components take up a rather large space, and can sometimes be as expensive as the measurement device to implement. In the miniaturization of the sensing devices, it makes little sense to use such a system, in terms of efficiency and cost. Significant benefits are gained if the sensing device and the sampling system can be integrated where the sample volumes are matched to the sensing device itself. Recent developments in industrial process improvement initiatives have been centered on the mechanism for integrating sensing devices into sampling systems. A good example is the New Sensors/Sampling Initiative (NeSSI) sponsored by the Center for Process Analytical Chemistry (CPAC) at the University of Washington, which is an effort by an industrial consortium to standardize sensors and the sensing platform used for process monitoring. Initially, traditional parameters such as temperature, flow and pressure, which can be important indicators of process characteristics, have been addressed. The goal for NeSSI implementation is to make measurement techniques uniform across industries with an interest in participating in the initiative. The platform is a miniaturized, modular version of traditional sample gathering and handling methodologies. Pursuant to the Instrumentation, Systems, and Automation Society (ISAS), standard SP76, establishes the interface of the sample gathering components with sensing devices used to assess the characteristics of the extracted sample. This standard defines both the function and requirements of the sensor system, and provides a specification for the interconnection of the sensor to the modular sensing system. This standard is now supported by all of the major components manufacturers that are suppliers to the industry.

The benefits of the NeSSI system are its size, the ability to add components as standard modules, and the ability to integrate the sensing system to form a single stand-alone unit for sample extraction, conditioning and measurement. The objective is to develop sensing devices that meet the interconnectivity protocols of NeSSI. What is also needed is such a system that enables sampling and sensing at intermediate sites along the way of the process, thereby permitting process corrections earlier and minimizing defective product output. Note that NeSSI has been used here as a discussion point, and is not necessarily the only platform for consideration. There is a movement in a wide variety of fields that involve the handling of liquids, gases and vapors, where miniaturized valves and sample handling/conditioning are involved. This can include miniaturized modular components and manifolds that are fabricated from materials such as plastics, and can include systems that are described as microfluidic sample handling systems. The approach to integration of the spectral sensing devices within these platforms is also important for key applications, such as water chemistry, environmental measurements, and clinical and medical applications.

SUMMARY OF THE INVENTION

It is an object of the present invention to provide an integrated spectral sensor. The term integrated is used to indicate that the device is to be fabricated as a single structure, where the components are intimately interconnected in a miniaturized platform. The system includes a sampling component, a spectral engine including a sensing component and a signal conditioner, a signal exchange system, and a controller, all assembled as a single structure. The interfacing optics form part of the structure, with no requirement for additional imaging elements such as lenses or mirrors, as used in spectrophotometers. The sampling component can include, where required a multi-port manifold on a miniaturized sample handling platform (such as NeSSI) for gathering one or more fluid samples (including reagents) related to the industrial process to be controlled. The sampling component interfaces with the spectral engine that includes an optical sensing system for nonintrusive detection of features of the sampled fluid. The spectral engine further includes a light or energy source, spectral sensing component, featuring a fully integrated spectrally selective detection device (described as a spectrometer or photometer on a chip), for measuring the characteristic chemical features of the fluid, a sample cell or chamber that is intimately connected to the source and sensing element, and is dimensionally optimized and matched to these components, and a microprocessor for conditioning the signals output from the spectral sensing element. Additional functions of the microprocessor include, spectral data extraction, and the calculation of chemical composition or properties, method and calibration storage, and data communications. The signal exchange system may be a wired or a wireless signal transfer device coupled locally or remotely to the sensor.

Four example application areas have been identified that can benefit from this integrated sensor approach, and these include the water, the pulp-and-paper, chemical, and petroleum industries. These applications require on-line, real-time sensors, sensors that are capable of operating in harsh environments, and can provide analytical and physical property measurements. The present invention addresses these needs, especially in combination with the NeSSI sampling platform. In the case of the chemical industry, a wide range of applications is envisaged in many industry sectors, from specialty chemicals, such as pharmaceutical products to commodity chemicals, such as petrochemicals and polymers. The applications go beyond just the manufacture of the raw materials and basic chemicals, and can be extended to the blending and formulation of final products in key high energy consuming industries, including those linked to consumer products, such as gasoline and other fuels. It is to be understood that the present invention has broader applicability than the application areas cited.

In conventional industrial process plants, process sensors and actuators are hardwired using copper wire or fiber optics networking. Because of the high costs associated with installation, maintenance, and constant reconfiguration of a process, there is a large opportunity for a major cost advantage for using a wireless communications path to interconnect the sensors and actuators. This is particularly important when a network of sensors is being employed. For this reason, the present invention contemplates the option of employing wireless connectivity to establish data signal transfer.

The integrated sample, sensing and control system of the present invention provides a more granular and immediate picture of relevant information associated with an industrial process. These and other advantages will become more apparent upon review of the following detailed description and the accompanying drawings.

DETAILED DESCRIPTION OF THE PREFERRED EMBODIMENTS OF THE INVENTION

Figure 1:
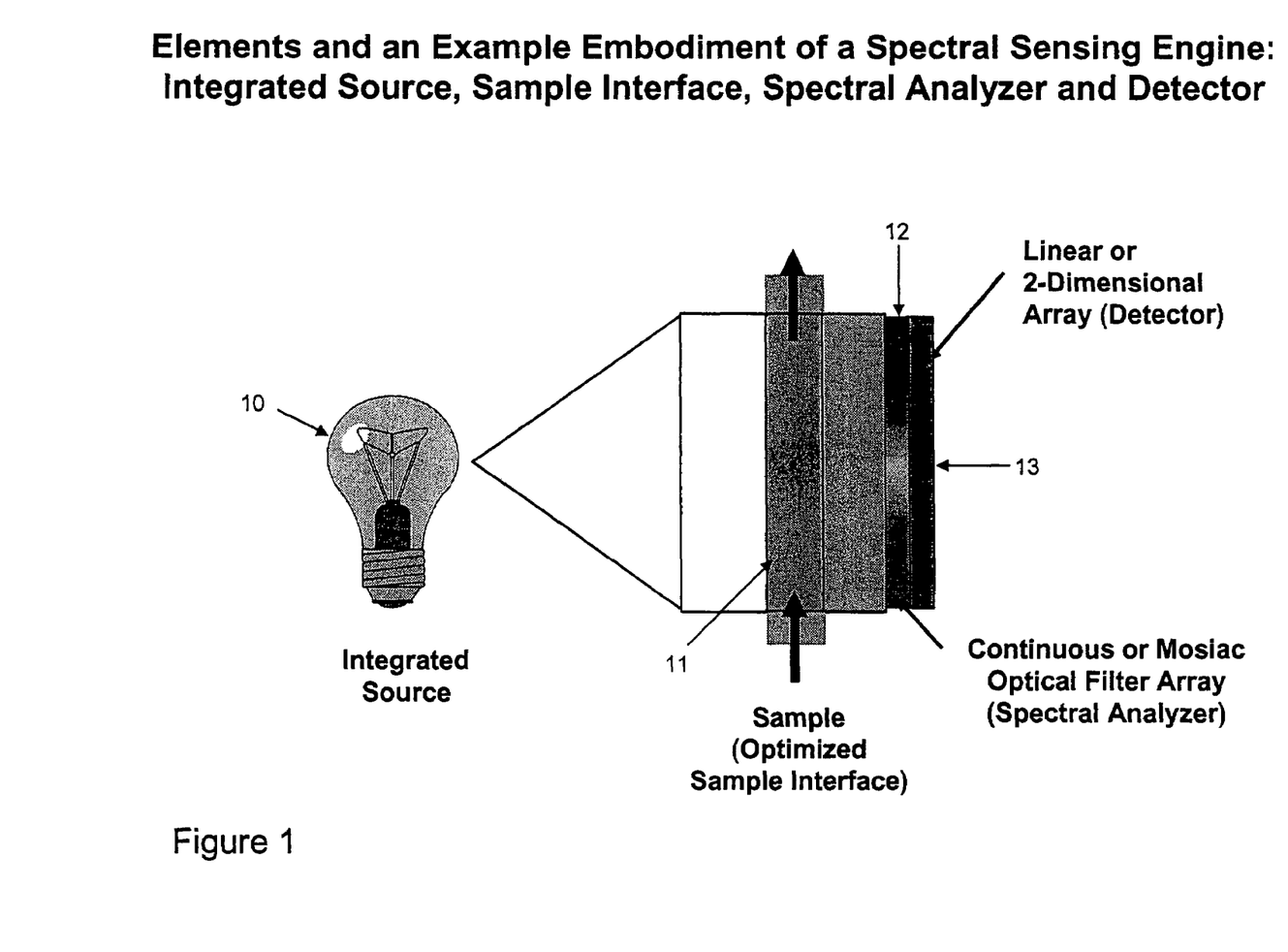
FIG. 1 is an example embodiment of a spectral sensing engine: integrated source, sample interface, spectral analyzer and detector.
Figure 4:
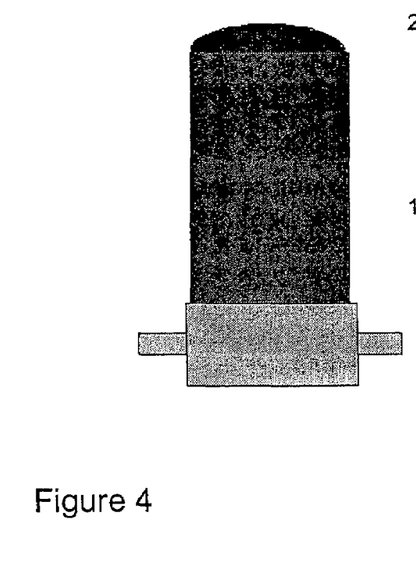
FIG. 4 are configurations for the preferred embodiments of on-line spectral sensors: absorbance/transmission and fluorescence cells.
Figures 4A, 4B:
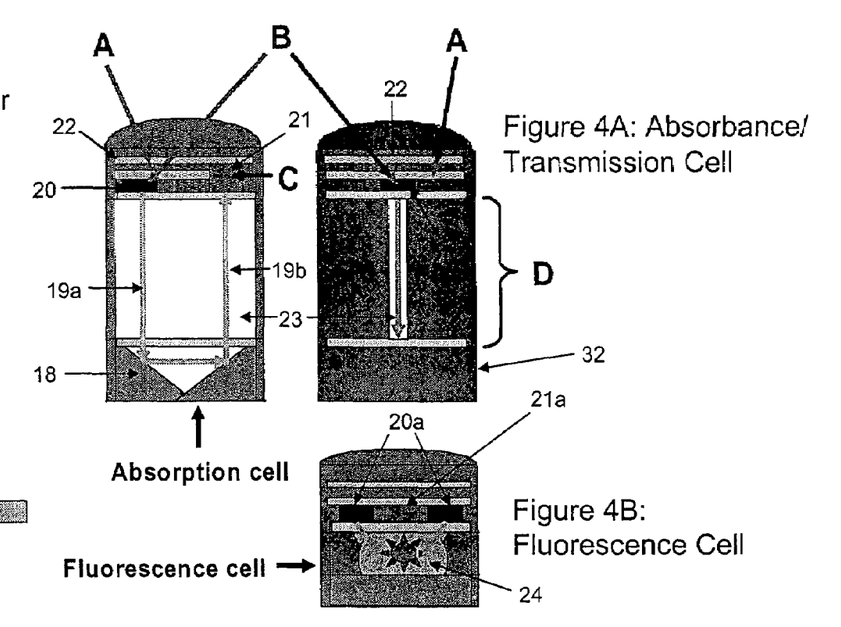
Figures 5A, 5B, 5C, 5D:
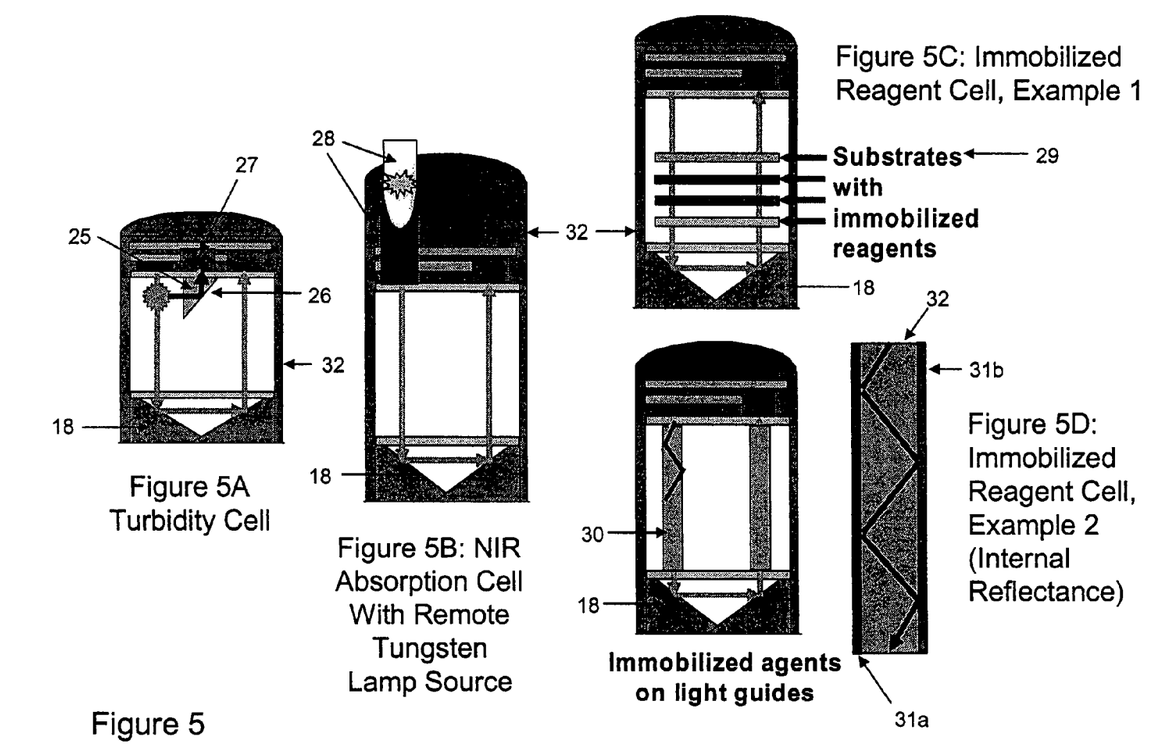
FIG. 5 are alternative configurations for the preferred embodiments of on-line spectral sensors: turbidity, NIR and immobilized reagent versions.
Figure 6:
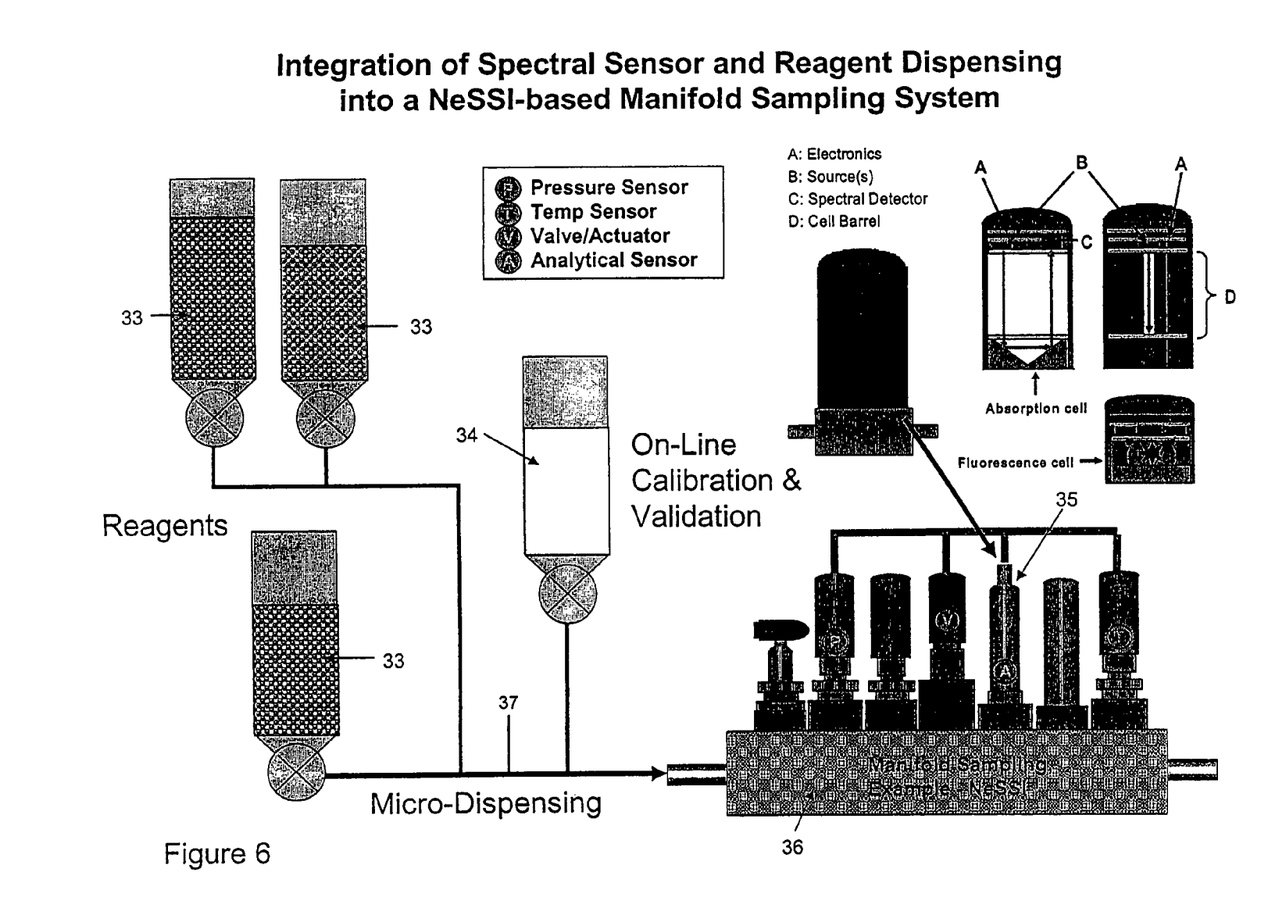
FIG. 6 is an example integration of spectral sensor and the reagent dispensing into a NeSSI-based manifold sampling system.

The present invention is an integrated measurement system for spectral sensing process characteristics and controlling the process based on the sensed information. The sensing aspect of the invention preferably includes one or more miniaturized optical spectral sensors located at multiple points within a process or an individual process unit. FIG. 1 provides a symbolic representation of an example spectral sensing system, comprising a light or energy source 10, an optimized and integrated sample chamber 11, a spectral analyzer or spectrally selective element 12, and an integrated detection system 13. Example embodiments of such spectral sensing systems are illustrated in FIGS. 4 and 5. The individual spectral sensors are integrated at multiple locations within a process by the use of a standardized modular sampling system (NeSSI being an example), as represented in FIG. 6. This provides a means to monitor a process from start to finish, with key intermediate points also covered, as opposed to the traditional approach of monitoring the product as it is produced at the end of the production line. An optional component of the system is a wireless communications interface, based on a standard wireless platform, associated with the multiple spectral sensors to allow them to interface with the control component of the process.

Figure 2A:
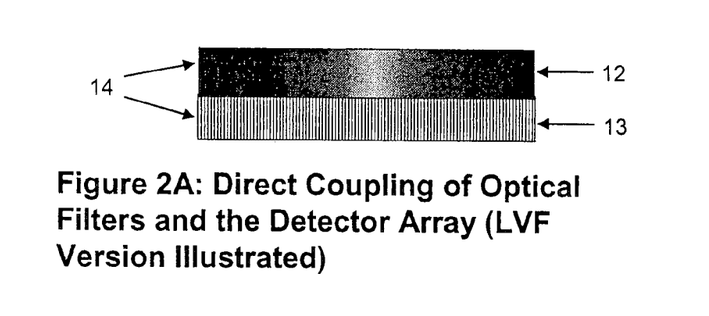
FIG. 2 are example combinations of optical filters and detector components used for spectral sensing.
Figure 2B:
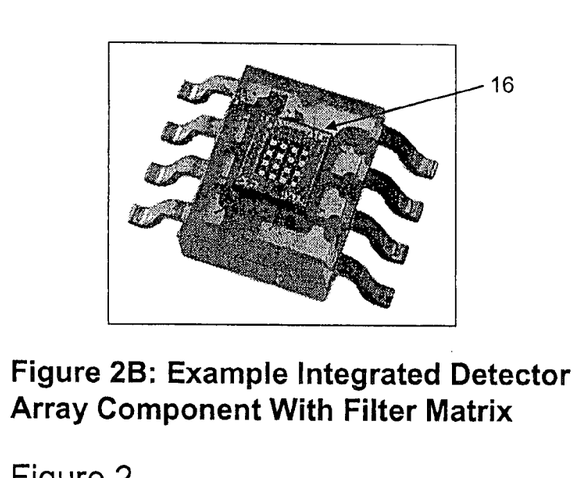
Figure 2C:
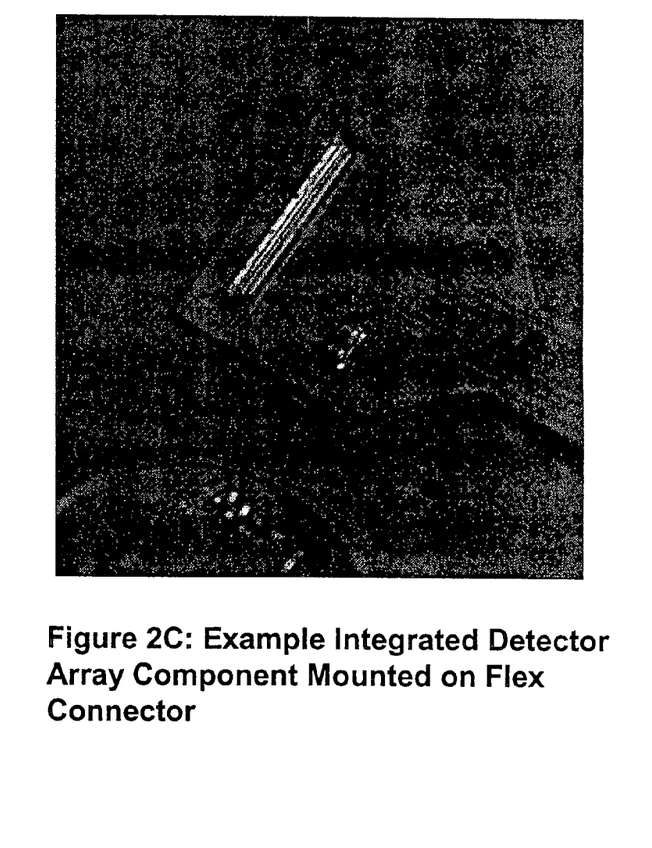
Figure 7:
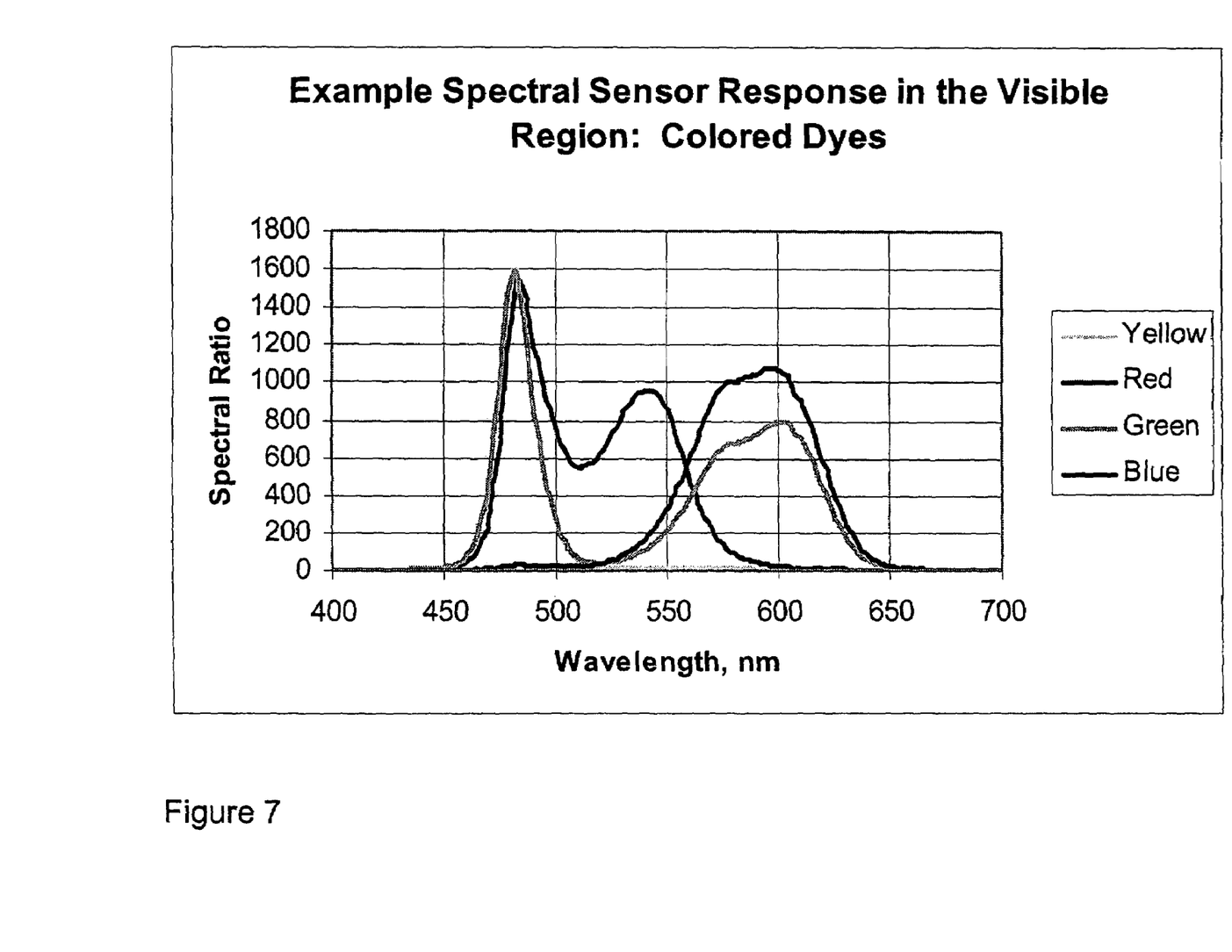
FIG. 7 is an example spectral sensor response in the visible region: colored dyes.
Figure 8:
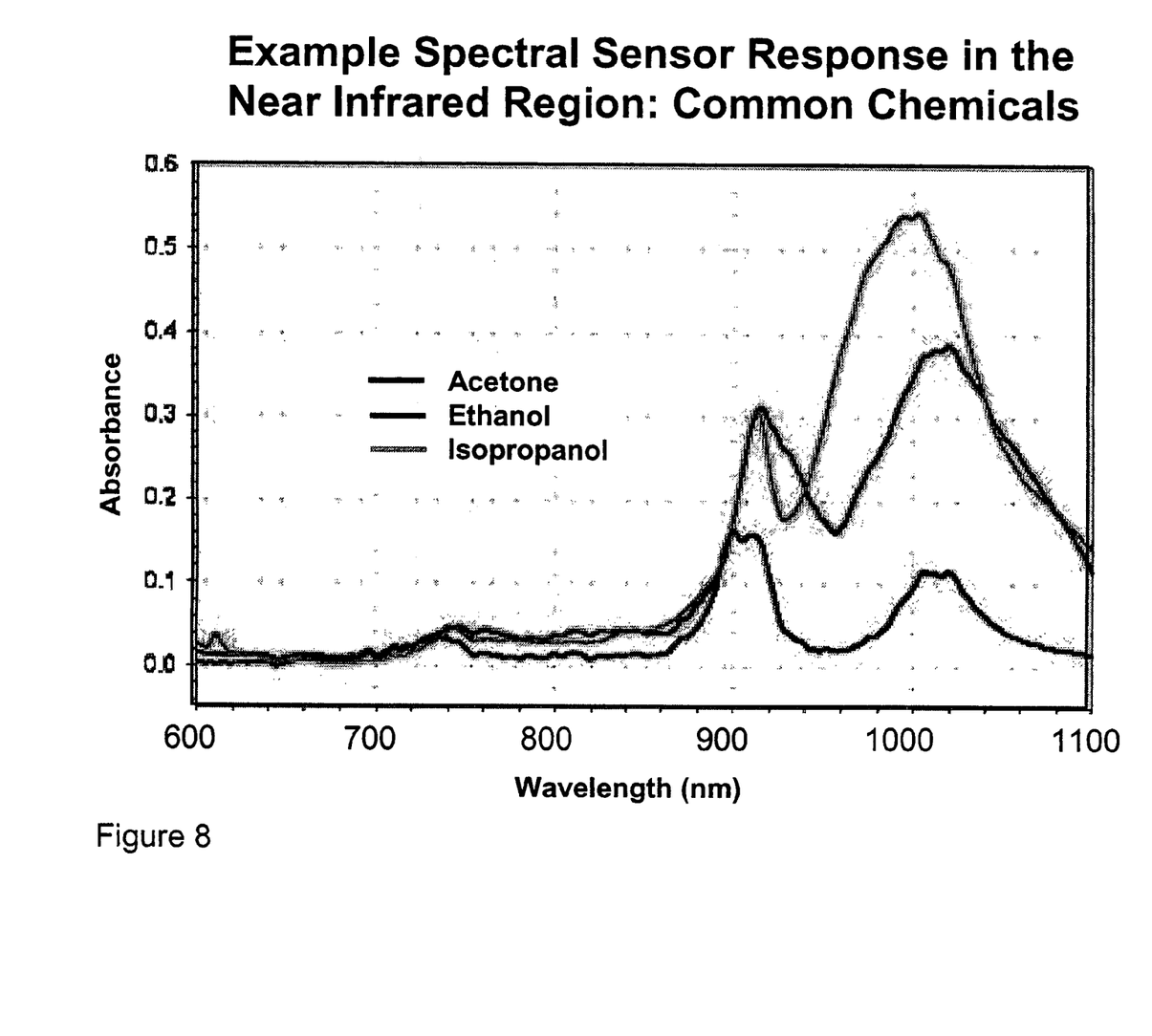
FIG. 8 is an example spectral sensor response in the near infrared region: common chemicals.

An important component of the spectral sensor technology can be broadly described as an optical spectrometer on a chip as represented in FIG. 2 by 14, 15 and 16. While optical sensors have been available, the present invention integrates an optical filter assembly 12 with a light or energy sensitive array 13. The optical filter technology used is either in the form of a continuous linear variable filter (LVF) 14, 15, or a filter array (patterned filter or mosaic) 16. In the LVF form, the resultant device, or spectral sensing component 14, 15, is the most versatile and can be utilized for many applications. An example format of an LVF-based spectral sensor is shown in FIGS. 1, 2A and 2C. The spectral sensing component is preferably implemented as part of a photodiode or a Complementary Metal-Oxide Semiconductor (CMOS) array detector package 15. In the current embodiment, the LVF is directly bonded to the detector array which preserves the spectral resolution of the LVF. In this form the assembly does not require any form of resolution retaining optics, as required with earlier implementations. Sensors derived from these components based on the LVF can be used for absorption measurements in the visible and near infrared (NIR), as well as fluorescence measurements in the visible. Examples of data have been acquired in all of these modes, and example spectral response curves for the visible and NIR ranges are provided FIGS. 7 and 8. The short wave NIR provides good differentiation based on chemistry and composition based on vibrational overtones of the component molecules. However, in cases, such as the digestions in pulp and paper applications, where visible absorbing and fluorescence centers are also expected to be important, the visible version for the spectral sensor is used. For applications involving chemistry, where the species to be measured is not normally visible, the analysis may be performed with the addition of a reactive chemical reagent 33 via the modular sampling system 36 as suggested in FIG. 6. The reagent may be added as an additional chemical to the process stream via a micro-dispensing system 37, or the process stream can interact directly with versions of the reagent that are immobilized on or in a solid substrate, which forms part of the optical path as shown in the examples in FIG. 5; 5C features a light transmission configuration, and 5D features an internal reflectance configuration.

Figure 3:
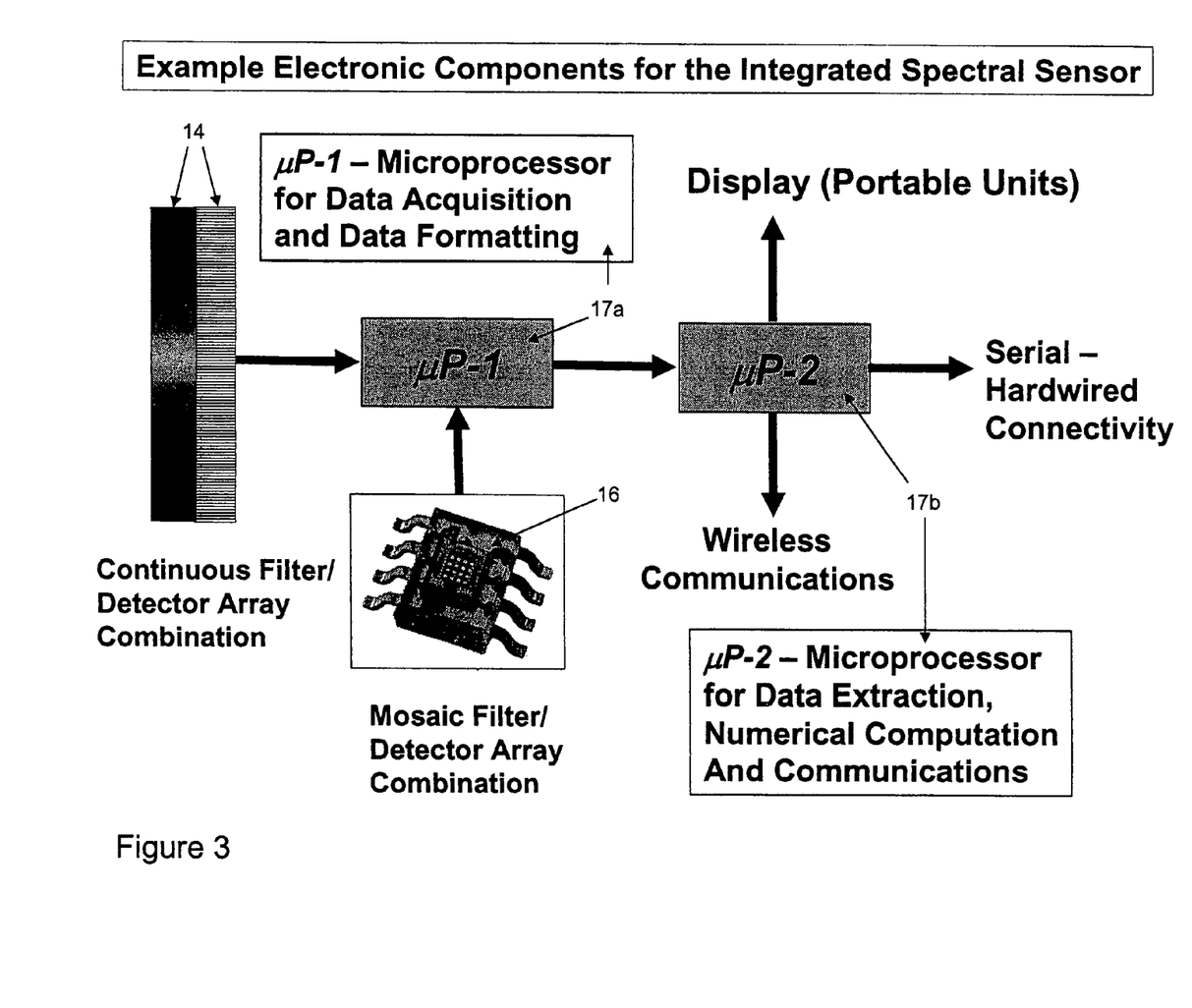
FIG. 3 are example electronic components for the integrated spectral sensor.

Those skilled in the art of optical sensing technology will recognize that the short-wave Near Infrared (700 to 1100 nm) works well for a wide range of liquid-based measurements. In this region, sample pathlengths from 1 to 10 cm are considered to be optimum, dependent on the material to be measured. Such pathlengths may be used for direct measurements made on petroleum and liquid chemical products, while shorter path lengths may be required for darker materials, such as digestion products and materials with high aromatic content. The pathlength is defined within the integrated construction of the sensor as part of the close-coupled sample chamber. In order to make the sensor a single-sided entity, suitable for coupling with the NeSSI-style sampling system, it is necessary to use a folded path construction, as illustrated in FIG. 4 (4A) and FIG. 5. This folded pathlength is obtained by the use of a retroreflective element located in the base of the sample chamber 18. Although spectral changes in this region are subtle, they can be readily correlated with both composition and key chemical and/or physical properties. Tools such as multivariate modeling, sometimes known as chemometrics are common for such applications. These would be used as appropriate, and the calibration coefficients generated from the modeling are stored on flash RAM associated with one or more microprocessors 17a and 17b, as shown in FIG. 3, located on-board the sensor. It is expected that the flash RAM will be either present as separate memory components, or integrated into the microprocessors.

It is also possible to consider indirect methods of measurement while measuring in this silicon spectral region. These are methods are as noted above, where a reagent interacts with the stream either as a liquid reagent or on a substrate that interacts with the process stream, and spectral changes are observed for the substrate (FIGS. 5C and 5D). Examples are pH (where an acid-base indicator is immobilized) or chemical reactivity of the stream, where the stream reacts with a reagent that is immobilized in a porous solid matrix, such as a sol gel or a membrane (organic or inorganic). In the case of the use of the internal reflectance-based systems, the immobilized reagent 31a and 31b is deposited directly on the surface of an optical light guide 30 as shown in FIG. 5. Note that the light guide can be rectangular in cross section and different immobilized reagents 31a and 31b can be deposited on opposing light guide surfaces 30. Systems featuring immobilized reagents can also be used for gas phase measurements where the gas or vapor is chemically reactive and is able to form a colored species once it interacts with the immobilized reagent. An example of such a reaction is with carbon monoxide and a derivative of hemoglobin. If the reaction is reversible, the sensor may be used for continuous monitoring. The resultant reaction is a color change or a change in a level of fluorescence. For non-reversible reagent chemistries the sensor can be used as an alarm sensor, where the immobilized sensor elements are disposable and replaceable. The optical sensor system of the invention may be used to conduct direct measurements (FIGS. 4, 5A and 5B), as well as with immobilized reagents necessary for applications in the water industry, and in the pulp industry, for example, especially for the measurement of materials such as sulfides, both in the liquid and gas phases (FIGS. 5C and 5D). For applications that feature liquid based reagents, the reagent or reagents are metered into a mixing chamber which would exist as one of the components of the manifold system, on the NeSSI substrate (manifold backbone). Applications based on chemical reagents do not necessarily require long optical pathlengths, and pathlengths ranging from 0.25 cm to 2.00 cm are expected to be the norm. The pathlength would be defined in the same manner as described above for near infrared, and would feature a folded pathlength generated by a retroreflective element 18.

As defined, the spectral sensor can be constructed from either a continuously variable filter (defined as the LVF) 14 or from a filter matrix or mosaic 15. This latter approach is usually optically more efficient and less expensive than the LVF approach. It is often more specific in application, but less versatile than the LVF system. An illustrated example of a matrix-based spectral sensor 16 is provided in FIGS. 2 and 3. The version shown is an 4-channel RGBW (Red-Green-Blue-White) sensing device, and is capable of handling a wide range of color-based applications.

The sensor hardware for the present invention is not limited to silicon-based photo-sensing devices, and alternative detector arrays can be used, including InGaAs, PbS, PbSe and also MEMS-based devices. Such devices would be considered for extensions into the longer wavelength NIR and for the mid-IR. The format of the proposed sensor platform may be extended into these other spectral regions. In the case of the mid-IR spectral region, these are expected to be mainly for gas and vapor phase applications. Note that for some applications, the silicon-based detectors may be used in conjunction with an immobilized reagent for certain gas-phase measurements. For example, vapor analysis for pulp digestions may be handled by this approach, especially for the detection of sulfides.

The approach offered is described as being based on a spectral engine (FIG. 1), which is further illustrated in its final proposed embodiments in FIGS. 4 and 5. The spectral engine includes the spectral sensing device (described above) 14 and 15 as shown in FIG. 3, and the energy source 10 as shown in FIGS. 1 and 20 as shown in FIG. 4, which can be either a broadband or narrowband source, dependent on the mode of measurement (broadband sources are used for NIR and visible absorption, narrowband sources are used for turbidity and fluorescence). White LEDs and tungsten bulbs are used as broadband sources, and individual LEDs and semiconductor laser devices are used as narrowband sources. In the case of the use of a tungsten bulb source, a combined assembly 28 (FIG. 5) featuring the bulb and a light guide can be used for situations where direct heat from the bulb would cause measurement or safety problems. Another component of the spectral engine is the sample interface, which is typically a cell or chamber 23 or 24 as shown in FIG. 4. One of the key benefits offered by the system is that the cell or chamber can be optimized in size based on the physical dimensions of the source and spectral sensing system. The sizes of the detection devices are, for example, 1 mm×8 mm 15 as shown in FIG. 2 and approximately 3 mm×3 mm (matrix sensor 16). Scaling the sample cell to these physical dimensions can produce sample cell (chamber) volumes as low as 80 microliters. The advantage gained here is that a minimum sample size is required, which effectively eliminates any sample temperature effects, and significantly reduces the amount of reagents that have to be dispensed for reagent-based applications. The volume requirement for reagents can be reduced down by as much as 1000 times, which reduces reagent storage vessel capacities, and dramatically reduces consumption and operating costs. The final critical set of components of the spectral engine is the electronics. An example of the functional electronics is provided in FIG. 3, which are physically located within the total sensor enclosure 32 as illustrated in FIGS. 4 and 5. As shown in FIG. 3, up to two microprocessors, and possibly more are proposed that handle the initial data handling (processor #1 17a) and then the data massaging (processor #2 17b). It is envisaged that the final processor 17b would feature onboard memory to store methods, calibrations and results, and would handle communications to displays (if required), external devices via serial connections and also wireless communications if the option is used.

It is known that measurements from industrial processes require a degree of sample conditioning. Normally this necessitates the use of a sampling system in conjunction with a process analyzer. The use of a traditional sampling systems would negate the cost and size benefits of the proposed sensor technology. For this reason, as shown in FIG. 6, the present invention combines the spectral sensing device 35 with a miniaturized sample handling platform 36. The NeSSI generation II platform is used as a practical example of a miniaturized modular approach to sample handling, based on a manifold 36, with the provision for modular sensor integration 35. The spectral sensors of the present invention can be designed to be compliant with the published specifications of the ISAS SP76 standard which defines the interface and format of the NeSSI platform. The specification dimensionally defines the interface between the sensor and the sampling system, and provides a preferred method for sealing the sensor on the modular interface backbone (also called the NeSSI substrate 36). The "footprint" occupied by the sensor is an area of approximately 1.5 inches by 1.5 inches. This is an important set of dimensions, because it also defines the nature and size of the overall structure, where a typical vertical dimension would be between 4 inches and 8 inches, dependent on the pathlength of the sample chamber, and the area occupied by the electronics. The sensors can also be designed to interface with any other form of miniaturized sample handling. For example, new micro-valve systems based on micro-technologies, and activated for example, by piezo-electric devices, and also micro-fluidics are considered as suitable components for alternative candidate sampling systems. Note that for NeSSI-based systems, as shown in FIG. 5, the sensor body/enclosure 32 will normally be constructed from machined metal parts. However, for applications based on aqueous chemistries, and for non-hazardous operating environments, molded plastic parts will be considered as options. This will include optical components for cases where the materials used will not pose a major spectral interference. For some applications, where plastics are used, the parts constructed can be considered to be disposable, interchangeable and readily replaceable.

The spectral sensor implementation based on NeSSI may be implemented in several ways. FIG. 6 provides a view of the sensing device integrated 35 into a modular base compliant with NeSSI 36. FIGS. 4 and 5 show example configurations for the spectral sensor that meet these requirements. This includes a basic transflectance (absorption/transmission) arrangement FIG. 4A wherein the source 20 radiation is directed into the sample chamber 19a, and the beam is reflected from the retroreflective base 18 of the module up into the sensing area 19b and on to the spectral sensing detection device 21, which is powered and controlled by onboard electronics board 22 in FIG. 4A. Note that the electronics is shown mounted horizontally 22, however the invention does not require the board to be mounted horizontally, and alternative configurations with a vertically mounted board, connected via a rigid connector, or a flex connector are included as design options. These electronics can be linked to an external network, which may include wired transmission or wireless telemetry. An alternative sensor configuration (see FIG. 4B) provides a geometry that can be used for fluorescence measurements or for dark samples, with an abbreviated sample chamber 24, and with an alternative configuration for the source 20a and spectral sensing detector 21a. FIG. 5 shows alternative arrangements that can be used for turbidity (see FIG. 5A), near-infrared (see FIG. 5B) for applications requiring an isolated, remote source, and also for applications involving immobilized agents (see FIGS. 5C and 5D). In the case of the turbidity measurement, an alternative light path is used 25, in conjunction with the normal light path 19a and 19b through the sample chamber as shown in FIG. 4. In this arrangement, scattered light from the sample is collected at 90 degrees 25 (see FIG. 5) to the normal light path 19a and 19b (see FIG. 4), and this is reflected back via a 45 degree optic 26 (see FIG. 5) to a secondary detection system 27. For NeSSI-based implementations, it will be normal for the body of the sensor, and other internal structural components (non-optical) to be constructed from machined metal parts, and often from materials such as 3/16 stainless steel.

The fundamental aspects of the present invention lead not only to increased productivity, but also to an energy saving and process efficiency capability in at least the four target industries: water, paper, chemical, and petroleum industries. In the case of water, it also leads to increased public safety. It is expected to provide similar advantages in consumer-oriented markets, including food and dairy processing, beverages, and household products (cleaners, etc.). The technology of the current invention will be particularly useful in the four noted fields of application:

Water application: continuous monitoring of public water supplies for residual chlorine content and similar parameters that are important to public safety. Residual Chlorine (disinfectant) is an important marker in drinking water supplies for the unexpected introduction of toxic and biohazard materials. The latter can range from the accidental introduction of bacteria via a breakage in a feeder pipe, to the deliberate introduction of dangerous materials. As shown in FIG. 6, active chlorine content is measured via a standard procedure defined by the EPA, and uses a commercially available reagent system 33, which can be integrated with a dosing system 37 within the modular sampling system interface 36. The system can also be configured to measure heavy metals (lead, chromium, mercury, etc.) and also environmental contaminants, such as phosphate, nitrate and arsenic. All of these chemical systems can be measured with standardized reagent systems as defined by the EPA. While the systems as described can be configured for public water supplies, stripped-down versions can also be configured for public buildings, office buildings, hospitals, and even residential water supplies. Such systems might include non-NeSSI manifold system, and could be based on the Microsystems outlined previously.

Petroleum applications: monitoring of process streams for raw materials, intermediates and final products. In an average refinery there are many process units, and many of these units have several critical points where measurements can be made. Examples include the reformer, cat crackers and the blenders. The convenience and cost potential of the invention may enable many more points to be monitored, thereby permitting a higher level of overall predictive control. Many of these processes are energy intensive, and so significant savings in terms of improvements in efficiency and reductions in environmental emissions are anticipated with the implementation of this technology. It is anticipated that the NIR versions of the spectral sensing system will be used for these applications.

Chemical applications: there are numerous potential applications for the invention in the chemical and petrochemical industries. These can range from the production of raw materials to various processes used in the pharmaceutical and biotechnology industries. It is anticipated that it is well suited for the petrochemical related industry, where a significant amount of energy is involved, and where good monitoring and control can provide better overall efficiency and product quality. A practical example is the production of carbon black, where the composition of the input hydrocarbon feed streams is used to provide additional information to the control system for the constrained combustion process used to manufacture this product.

Pulp and paper products: there are several potential areas of application for the present invention in the pulp and paper industries. The most important, from the point of view of control, are probably in the digestion, pulping, and bleaching areas. The use of NIR for the measurement of parameters such as Kappa has already been demonstrated, and the use of visible methods is feasible for determining lignin-related information. Another important area is bleaching. Both direct methods involving NIR, and indirect methods, involving immobilized agents are expected to work for this application. Control of both the digestion and the bleaching are important for the overall process, and good control parameters for digestion are expected to provide important energy savings.

While the present invention has been described with particular reference to certain specifically described components and methods, it is to be understood that it includes all reasonable equivalents thereof.

Having thus described the invention, what is claimed is:

1. An integrated spectral sensing system, comprising:
   a spectral engine comprising an optical filter assembly bonded to an energy sensitive array, the optical filter assembly and energy sensitive array collectively configured to sense energy transmitted through the optical filter assembly and to generate data based on the sensed energy;
   an energy source for generating energy for impingement upon the spectral engine;
   a sample interface comprising a chamber for containing a sample, sized and configured to match the size and configuration of the spectral engine and the energy source, disposed between the spectral engine and the energy source, and configured so that energy from the energy source passes through the sample and impinges upon the spectral engine;
   means for collecting, manipulating, and storing data generated by the energy sensitive array; and
   means for communicating the collected data.

2. The integrated spectral sensing system of claim 1 further comprising means for correlating at least a portion of the collected data with data representing chemical and/or physical properties.

3. The integrated spectral sensing system of claim 1, wherein the optical filter assembly comprises a continuous linear variable filter.

4. The integrated spectral sensing system of claim 1, wherein the optical filter assembly comprises a filter array.

5. The integrated spectral sensing system of claim 4, wherein the filter array comprises a patterned filter.

6. The integrated spectral sensing system of claim 4, wherein the filter array comprises a mosaic filter.

7. The integrated spectral sensing system of claim 1, wherein the energy sensitive array comprises a photodiode.

8. The integrated spectral sensing system of claim 1, wherein the energy sensitive array comprises a complementary metal-oxide semiconductor.

9. The integrated spectral sensing system of claim 1, wherein the energy source comprises a white LED or a tungsten bulb.

10. The integrated spectral sensing system of claim 1, wherein the energy source comprises an LED.

11. The integrated spectral sensing system of claim 1, wherein the sample interface is configured to comply with NeSSI.

12. The integrated spectral sensing system of claim 1, wherein the sample interface is configured to comply with ISAS standard SP76.

* * * * *